United States Patent [19]

Semple et al.

[11] 3,973,277

[45] Aug. 10, 1976

[54] ATTACHING FIBROUS CONNECTIVE TISSUE TO BONE

[76] Inventors: James Campbell Semple, 59 Hamilton Drive, Glasgow G.12, Scotland; Gordon Arthur William Murray, 14 W. End, Long Whatton, Loughborough, Leics. LE12 5DW, England

[22] Filed: Jan. 23, 1975

[21] Appl. No.: 543,625

[30] Foreign Application Priority Data
Jan. 30, 1974 United Kingdom................. 4280/74

[52] U.S. Cl............................................. 3/1; 3/1.9; 128/92 C
[51] Int. Cl.²......................................... A61F 1/24
[58] Field of Search......................... 3/1, 1.9–1.913; 128/92 C, 92 CA, 92 E; 32/10 A; 206/363, 368–370

[56] References Cited
UNITED STATES PATENTS

| | | | |
|---|---|---|---|
| 2,857,670 | 10/1958 | Kiernan | 32/10 A |
| 3,314,420 | 4/1967 | Smith et al. | 3/1 UX |
| 3,500,829 | 3/1970 | Abramowitz | 206/363 X |
| 3,513,484 | 5/1970 | Hausner | 3/1 |
| 3,745,590 | 7/1973 | Stubstad | 3/1.9 |
| 3,852,045 | 12/1974 | Wheeler et al. | 3/1 |

FOREIGN PATENTS OR APPLICATIONS
1,083,769  9/1967  United Kingdom............... 128/92 C

*Primary Examiner*—Ronald L. Frinks
*Attorney, Agent, or Firm*—Baldwin, Wight & Brown

[57] ABSTRACT

A bone implant for attaching fibrous connective tissue such as a tendon or ligament, either artificial or natural, to bone, which comprises a tapered porous plug, preferably of sintered metal; a tendon prosthesis having such a plug at its distal end is also disclosed.

12 Claims, 3 Drawing Figures

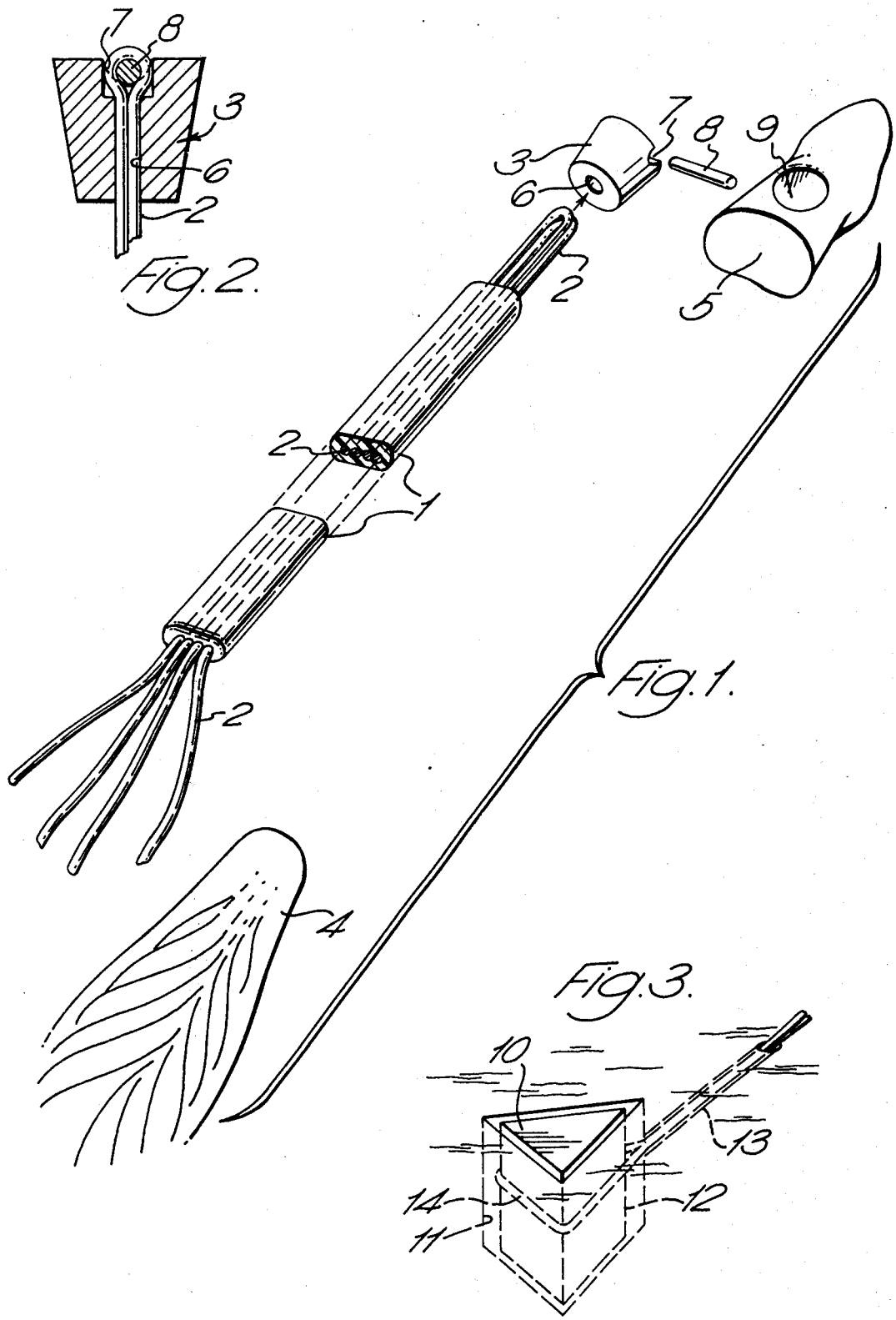

ATTACHING FIBROUS CONNECTIVE TISSUE TO BONE

This invention relates to improvements in attaching fibrous connective tissue to bone, and in particular to tendon and ligament prostheses.

It has been proposed to replace a tendon by either directly grafting in place a tendon from a less important part of the body or by employing an artificial tendon such as a cord of an inert plastics material. To directly graft in place a tendon from another part of the body can cause adhesions between the grafted tendon and the surrounding tissue. This leads to a consequent loss of mobility. Problems have also arisen over securing tendon prostheses to the bone and the muscle (especially the former) with sufficient strength to withstand long term use.

One major problem is providing a sufficiently strong securing means between the fibrous connective tissue and the bone. Various methods have been devised for anchoring tendon prostheses: many of these methods have involved mesh-like materials which are employed to enable tissue infiltration into the mesh to occur so as to provide a strong bond. These methods are discussed, for example, in U.S. Pat. No. 3,805,300. It is also known to construct certain bone implants using porous material, the pores facilitating anchorage of the bone to the implant as a result of bone growth into the pores (see U.S. Pat. No. 3,808,606). At present, however, there is still a need for improved means for connecting fibrous connective tissue to bone.

According to the present invention there is provided a bone implant for attaching fibrous connective tissue (either artificial or natural), such as a tendon or ligament, to bone, which implant comprises a tapered porous plug.

The reason for tapering the plug is to provide intimate contact of plug and bone by action of the tension in the fibrous tissue. During the healing process, this intimate contact will promote the ingrowth of calcified bone rather than soft tissue by restricting or stopping movement of the plug relative to the surrounding bone.

In a preferred aspect of the invention there is provided a tendon prosthesis provided at its distal end thereof with a bone implant in accordance with the invention.

In use in a tendon prosthesis the plug is located in a corresponding recess in the bone at the distal end of the tendon prosthesis and the end of the prosthesis remote from the plug is laced to the proximal tendon or muscle. Since the plug is porous, in time, bone tissue grows into and through the voids in the plug and this provides a very secure attachment for the tendon prosthesis to the bone. The plug is tapered and attached to the remainder of the prosthesis so that, in use, the plug is held in tension in the direction of the taper. With this arrangement the tapered plug is held firmly in its bone resection. The plug may be formed of any biocompatible material, for example a suitable ceramic, metal, or plastics material. Since it is porous, a convenient method for its manufacture is by sintering ceramic, metal, or plastics particles into a suitable tapered form. Preferably the plug is of sintered metal, especially sintered titanium, niobium, or tantalum, or an alloy containing one or more thereof. In one preferred method of manufacture, titanium wire of 20 to 200 microns diameter is wound around on a fine mandrel to provide a coil, pulled off the mandrel and extended so as to produce a series of helical regions. This wire is then packed into a suitably-shaped die, compacted, and heated in a vacuum or inert gas so as to sinter the wire into a compact body. Preferably as many pores as possible in the sintered body should have a diameter or width of 100 to 400 microns. Winding the wire on the mandrel and extending it as described above avoids forming dense regions in the structure.

The fibrous connective tissue may be connected to the plug by any suitable means. A ligament can be looped around and tied to the plug, for example as described hereinafter. The replacement for the original fibrous connective tissue in a tendon prosthesis can be attached to the plug by adhesive or it can be formed integrally therewith. Preferably, however, specific means are provided for anchoring the fibrous connective tissue to the plug, for example by providing a pin which extends transversely of the connective tissue and locates in a recess the plug. For a tendon prosthesis, the plug is preferably frusto-conical. The plug may be provided with a passageway to receive an end of the fibrous connective tissue.

The tendon prosthesis of the invention, in addition to the bone implant described above, is preferably provided with a cord member having its central portion coated or sheathed with a material to promote sliding movement of the cord member within the body.

The cord member will generally be substantially non-resilient and may be, for example, of braided form, a monofilament, or even strip-like. Preferably, it is an inert synthetic plastics material, such as a polyester or a polyamide thread.

The sheath or coating for the cord member may be of any appropriate inert material (such as synthetic plastics material) and may be of any cross-section appropriate to the cross-section of the cord member, for example, annular. A sheath member may be, for example, a right cylindrical silicone polymer of polyurethane tube. The sheath or coating acts as a barrier against adhesions between the cord member and the surrounding tissue and hence promotes sliding movement of the cord member in the body.

Preferred features of the invention will now be described, by way of example, with reference to the accompanying drawing in which:

FIG. 1 is a schematic representation of a tendon prosthesis of the invention in place in the body between a muscle and the distal phalanx of a finger in a hand.

FIG. 2 is a cross-section of the plug shown in FIG. 1 with the cord member and pin in place, and FIG. 3 is a schematic perspective view of a bone implant according to the invention in use in securing a ligament to bone.

Referring to FIG. 1, the tendon prosthesis comprises a polyurethane coating 1, a cord member 2 consisting of four strands of polyethylene terephthalate filament, and a plug 3. The tendon extends between a muscle-tendinous junction 4 and the bone of the distal phalanx 5.

The plug 3 is formed by sintering together through wires and is porous to the extent that approximately 50% of its apparent volume is constituted by voids. The plug 3 is frustoconical and is provided with a axial bore 6 through which the cord member passes and a recess 7 in which is located a locking pin 8. The locking pin 8 is transverse to the cord member and the cord filaments double around the pin 8, so that the ends of the filaments are remote from the plug. This arrangement prevents the cord member from pulling throgh the axial bore 6 in the direction of muscle 4 and provides an attachment between the cord and the plug of great strength and small volume.

A resection 9 is provided in the distal phalanx 5 to provide a close fit with the plug 3. The strands of the cord member 2 remote from the plug are separated, are passed through the musculo-tendinous junction 4, and are then laced thereto.

Referring to FIG. 2, it will be seen that the axial bore 6 is counter-bored from the surface adjacent recess 7 so as to accommodate the loop which is formed when the cord member 2 is doubled around the pin 8.

FIG. 3 shows a plug 10 which is generally wedge-shaped and which is inserted in the bone resection 11 with the thin edge 12 of the wedge lying axially within the resection. A bore 13 is provided through the bone adjacent the thin edge 12 so as to take the end of a ligament 14 which is looped and tied around the plug 10. The bore is taken to the thin edge of plug in such a manner that in use the tension on the plug is in the direction of the wedge-taper.

Since the bone implants and tendon prosthesis of this invention are placed in the body surgically, it is desirable that they be supplied in sterile, sealed packages. It may be convenient to include in each package an appropriate reamer for resecting the bone to receive the plug.

We claim:

1. A prosthesis which comprises artificial fibrous connective tissue and, at a distal end of said tissue, a bone implant comprising a tapered porous plug, said plug being connected to said artificial tissue with said plug tapering in the direction towards said artificial tissue.

2. A prosthesis according to claim 1 wherein the plug is provided with a passageway to receive an end of the fibrous connective tissue, means being provided to anchor the end of the fibrous connective tissue to the plug.

3. A prosthesis according to claim 2 wherein the anchor means comprises a pin.

4. A prosthesis according to claim 3 wherein the plug is provided with a recess extending across one face thereof, transversely of the passageway, for receiving the pin.

5. A prosthesis according to claim 1 wherein the plug is of frusto-conical shape.

6. A prosthesis according to claim 1 wherein the plug is of sintered metal.

7. A prosthesis according to claim 1 wherein said artificial tissue comprises a cord member, the central portion of the cord member being sheathed or coated with a material to promote sliding movement of the cord member within the body.

8. A prosthesis according to claim 1 wherein said plug is in the form of an elongated triangular cross sectional member.

9. A method of attaching fibrous connective tissue, either artificial or natural, to bone, which comprises, not necessarily in the following sequence, providing a tapered porous plug, providing a resection in the bone to receive the plug snugly, inserting the plug into the resection, and anchoring the fibrous connective tissue to the plug with the taper of said plug extending in the direction of said tissue so that, in use, the fibrous connective tissue pulls on the plug in the direction of the taper.

10. A method according to claim 9, wherein the plug is of sintered metal and of frusto-conical shape having an axial passageway therethrough, the fibrous connective tissue being passed through the passageway and being anchored to the plug by means of a pin disposed transversely of said passageway.

11. A bone implant for attaching artificial fibrous connective tissue to bone, which implant comprises a tapered porous plug having remote ends including a large end and being provided with a passageway disposed in the direction of said taper between said ends to receive an end of fibrous connective tissue, and pin means for extending transverse to said passageway in bridging relation thereto at said enlarged end to anchor a fibrous connective tissue end to said plug.

12. A bone implant according to claim 11 wherein said plug is provided with a recess extending across said large end transversely of said passageway for receiving said pin.

* * * * *

UNITED STATES PATENT AND TRADEMARK OFFICE
CERTIFICATE OF CORRECTION

PATENT NO. : 3,973,277
DATED : August 10, 1976
INVENTOR(S) : Semple, James Campbell et al It is certified that error appears in the above-identified patent and that said Letters Patent are hereby corrected as shown below:

In Column 2, Line 39, "of" should read --- or ---.

In Column 2, Line 61, "through" should read --- titanium ---.

In Column 3, Line 2, "throgh" should read --- through ---.

Signed and Sealed this twenty-sixth Day of July 1977

[SEAL]

Attest:

RUTH C. MASON
*Attesting Officer*

C. MARSHALL DANN
*Commissioner of Patents and Trademarks*